US 7,196,062 B2

(12) United States Patent
Kaufman et al.

(10) Patent No.: US 7,196,062 B2
(45) Date of Patent: Mar. 27, 2007

(54) METHOD FOR TREATING GLAUCOMA

(75) Inventors: Paul L. Kaufman, Madison, WI (US);
Benjamin Geiger, Rehovot (IL);
Alexander Bershadsky, Rehovot (IL);
Teresa Borras, Chapel Hill, NC (US)

(73) Assignees: Wisconsin Alumni Research Foundation, Madison, WI (US); Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 11/060,914

(22) Filed: Feb. 18, 2005

(65) Prior Publication Data

US 2005/0261184 A1 Nov. 24, 2005

Related U.S. Application Data

(60) Provisional application No. 60/545,722, filed on Feb. 18, 2004, provisional application No. 60/545,723, filed on Feb. 18, 2004.

(51) Int. Cl.
*A61K 38/00* (2006.01)
(52) U.S. Cl. ...................................... 514/12
(58) Field of Classification Search .................. 514/12
See application file for complete search history.

(56) References Cited

U.S. PATENT DOCUMENTS

| 5,798,380 | A | 8/1998 | Kaufman et al. |
| 6,110,912 | A | 8/2000 | Kaufman et al. |
| 6,555,107 | B2 | 4/2003 | Poeschla et al. |
| 6,586,425 | B2 | 7/2003 | Kaufman et al. |
| 2002/0045585 | A1 | 4/2002 | Kaufman et al. |

OTHER PUBLICATIONS

Andrawiss, M., et al., "Adenovirus-mediated gene transfer in canine eyes: a preclinical study for gene therapy of human uveal melanoma," J. Gene. Med., 3:228-239 (2001).
Borras, T., et al., "Ocular adenovirus gene transfer varies in efficiency and inflammatory response," Invest Ophthalmol. Vis. Sci., 37:1282-1293 (1996).
Borras, T., et al., "Gene transfer to the human trabecular meshwork by anterior segment perfusion," Invest Ophthalmol Vis Sci., 39:1503-1507 (1998).
Borras, T., et al., "Adenoviral reporter gene transfer to the human trabecular meshwork does not alter aqueous humor outflow. Relevance for potential gene therapy of glaucoma" Gene her 6:515-524 (1999).
Borras, T., et al., "Non-invasive observation of repeated adenoviral GFP gene delivery to the anterior segment of the monkey eye in vivo," J. Gene. Med., 3:437-449 (2001).
Borras, T., et al., "Gene Therapy for Glaucoma: Treating a Multifaceted, Chronic Disease," Invest. Ophthalmol. Vis. Sci., 43:2513 (2002).

Budenz, D., et al., "In vivo gene transfer into murine corneal endothelial and trabecular meshwork cells," Invest. Ophthalmol. Vis. Sci., 36:2211-2215 (1995).
Hauswirth, W. & Beaufrere, L., "Ocular Gene Therapy: Quo Vadis?," Invest. Ophthalmol. Vis. Sci., 41:2821-2826 (2000).
Helfman, D., et al., "Caldesmon inhibits non-muscle cell contractility and interferes with the formation of focal adhesions," Mol. Biol. Cell, 10:3097-3112 (1999).
Kee, C., et al., "Stromelysin gene transfer into cultured human trabecular cells and rat trabecular meshwork in vivo," Invest. Ophthalmol. Vis. Sci., 42:2856-2860 (2001).
Loewen, N., et al., "Preservation of Aqueous Outflow Facility after Second-Generation FIV Vector-Mediated Expression of Marker Genes in Anterior Segments of Human Eyes," Invest. Ophthalmol. Vis. Sci. 43:3686-3690 (2002).
Loewen, N., et al., "Long-Term, Targeted Genetic Modification of the Aqueous Humor Outflow Tract Coupled with Noninvasive Imaging of Gene Expression In Vivo," Invest. Ophthalmol. Vis. Sci. 45:3091-3098 (2004).
Loewen N., et al., "Long-term retinal transgene expression with FIV versus adenoviral vectors," Mol Vis., 10:272-280 (2004).
Nakamura, Y., et al., "Signaling mechanism of TGF-beta1-induced collagen contraction mediated by bovine trabecular meshwork cells," Invest. Ophthalmol. Vis. Sci. 43:3465-3472 (2002).
Gabelt, B.T., et al., "Outflow Facility Enhancement By Caldesmon Gene Therapy In Organ-Cultured Human and Monkey Eyes," Invest Ophthalmol Vis Sci 45: E-Abstract 1032 (2004).
Haxhinasto, Kari, et al., "Gene Delivery of l-caldesmon Protects Cytoskeletal Cell Membran Integrity Against Adenovirus Infection Independently of Myosin ATPase and Actin Assembly" Am J Phsiol 287:C1125-C1138 (2004).
Liu, Xuyang, et al., "Herpes Simplex Virus Mediated Gene Transfer to Primate Ocular Tissues," Exp. Eye Res. 69, 385-395 (1999).
Santas, Amy J., et al., "Effect of Heparin II Domain of Fibronectin on Aqueous Outflow in Cultured Anterior Segments of Human Eyes," Investigative Ophthalmology & Visula Science vol. 44, No. 11 (Nov. 2003).
Geroski & Edelhauser, "Drug delivery for posterior segment eye disease," Invest. Ophthlamol. Vis. Sci. 41:961-964 (2000).
Fialho & da Silva-Cunha, "New vehicle based on a microemulsion for topical ocular administration of dexamethasone," Clin. Experiment. Ophthalmol. 32:626-632 (2004).
Friedberg et al., "Device drug delivery to the eye. Collagen shields, iontophoresis, and pumps," Ophthalmology 98:725-732 (1991).
Isowaki et al., "Drug delivery to the eye with a transdermal therapeutic system," Biol. Pharm. Bull. 26:69-72 (2003).
Pijls et al., "Studies on a new device for drug delivery to the eye," Eur. J. Pharm. Biopharm. 9:283-288 (2005).

*Primary Examiner*—Robert A. Wax
*Assistant Examiner*—Agnes B. Rooke
(74) *Attorney, Agent, or Firm*—Quarles & Brady LLP

(57) ABSTRACT

A method for reducing intraocular pressure and increasing outflow facility from an eye of a subject having glaucoma includes the step of providing in the trabecular meshwork of the eye an amount of caldesmon effective to reduce intraocular pressure and increase outflow facility.

3 Claims, No Drawings

METHOD FOR TREATING GLAUCOMA

CROSS-REFERENCE TO RELATED APPLICATIONS

This application claims the benefit of U.S. Provisional Patent Application Nos. 60/545,722 and 60/545,723, both filed Feb. 18, 2004. Each provisional application is incorporated by reference in its entirety as if set forth herein.

STATEMENT REGARDING FEDERALLY SPONSORED RESEARCH OR DEVELOPMENT

This invention was made with United States Government Support awarded by the following agency:
NIH, Grant Number EY02698.
The United States Government has certain rights in this invention.

BACKGROUND OF THE INVENTION

The present invention relates to treating ocular disorders and more particularly to treating glaucoma. U.S. Pat. Nos. 5,798,380, 6,110,912, and 6,586,425, each of which is incorporated herein by reference as if set forth in its entirety, describe in detail the nature and etiology of glaucoma and various therapeutic approaches for reducing intraocular pressure characteristic of the disorder. The incorporated patents disclose methods for enhancing aqueous humor outflow and reducing intraocular pressure in the eye of a subject by administering at least one non-corneotoxic ophthalmic preparation which can comprise at least one macrolide. Additional therapeutic modalities employing other agents are still sought.

Caldesmon, a protein found in smooth muscle and non-muscle cells, causes secondary degeneration of the actin-microfilament network and thereby interferes with actomyosin contractility and with formation of focal cell adhesions. Helfman, D. M., et al., "Caldesmon inhibits non-muscle cell contractility and interferes with the formation of focal adhesions," MBC 10:3097 (1999), incorporated herein by reference as if set forth in its entirety. Caldesmon, which contains actin-, myosin-, tropomyosin-, and $Ca^{2+}$-calmodulin-binding domains, inhibits an ATPase activity of actomyosin, blocks the interaction of actin with myosin, prevents myosin II-dependent cell contractility, and induces a decrease in number and size of tyrosine-phosphorylated focal adhesions. In the absence of calcium-calmodulin, caldesmon binds filamentous actin ("F-actin"). While various activities of caldesmon are known in general, there is no prior indication of advantageous drainage-enhancing and pressure-reducing activities by caldesmon in animal eyes.

A nucleic acid sequence that encodes caldesmon in humans is known and is disclosed at GenBank at Accession Number NM_033138 (variant 1), provided herein at SEQ ID NO:1 with the encoded caldesmon protein (from nucleotides 460–2838) being provided at SEQ ID NO:2. Several known transcription variants employ the same underlying nucleic acid sequence and are accessible at Accession Numbers NM_004342 (variant 2; coding portion from nucleotides 460–2076), NM_033157 (variant 3; coding portion from nucleotides 460–2154), NM_033139 (variant 4; coding portion from nucleotides 214–1890) and NM_033140 (variant 5; coding portion from nucleotides 214–1812). Variants 2–5 are expressed principally in non-muscle tissues, while variant 1 is expressed principally in muscle. The UniGene accession number for human caldesmon is Hs.490203. Other caldesmon-encoding sequences are known. For example, a nucleic acid sequence that encodes caldesmon in rat is known and is disclosed at GenBank at Accession Number NM_013146 (version 2). The sequence of NM_013146 (version 2) is provided herein at SEQ ID NO:3 with the encoded rat caldesmon protein (coding portion from nucleotides 156–1751) being provided at SEQ ID NO:4.

BRIEF SUMMARY OF THE INVENTION

In one embodiment, the present invention describes a method for reducing elevated intraocular pressure or increasing the reduced aqueous humor outflow facility associated with open angle glaucoma in a human or non-human subject having trabecular meshwork cells and having resistance to fluid drainage and intraocular pressure elevated above that considered clinically normal, the method including the step of delivering into the trabecular meshwork cells an ophthalmic preparation that comprises a non-corneotoxic delivery vehicle and a chemical agent, namely caldesmon.

In a related embodiment, the method includes the step of delivering into the trabecular meshwork cells an ophthalmic preparation that comprises an expressible caldesmon-encoding nucleic acid operably linked to a transcriptional promoter active in the trabecular meshwork cells so that expression of the caldesmon protein in the subject is facilitated after administration.

In either embodiment, the methods provide in and in the vicinity of the trabecular meshwork cells an amount of caldesmon sufficient to perturb cellular contractility by inhibiting actin-dependent myosin II ATPase and, perhaps secondarily, cell adhesions, mainly by reducing tension forces generated by the adhesion-associated cytoskeletal structures that are necessary to maintain adhesion. Reduced contractility and/or perturbation of these adhesions reduces resistance of the trabecular meshwork to fluid flow, enhances aqueous humor outflow from the eye and thereby treats the glaucoma by reducing intraocular pressure in a therapeutically useful manner. However, an understanding of the mechanisms (e.g., the specific molecular mechanisms) is not necessary to utilize the present invention. Indeed, it is intended that the present invention not be limited to any particular mechanism(s).

In either embodiment, the preparation can optionally further include one or more additional non-corneotoxic agents for reducing intraocular pressure and increasing outflow facility or for such other purpose as may be convenient in a particular case. The delivery vehicle can be conventional, and can include standard salt solutions and preservatives for topical administration, or aqueous or salt solutions without preservatives for intracameral or intracanicular administration.

The technical methods for delivering the caldesmon to the eye, and more particularly to the cells of the trabecular meshwork of the eye, can be conventional and are within the level of skill in the art. In particular embodiments, the administration method is topical delivery to the trabecular meshwork cells. In other embodiments, the administration method is intracameral delivery. In still further embodiments, the administration route is intracanalicular. In addition, the present invention provides compositions and methods suitable for relaxing actomyosin, the potent contractile machinery that includes actin and myosin filaments.

The present invention provides effective and, in some cases, non-invasive methods for treating glaucoma without causing untoward and unacceptable adverse effects, such as corneal edema.

BRIEF DESCRIPTION OF THE SEVERAL VIEWS OF THE DRAWINGS

Not applicable.

DETAILED DESCRIPTION OF THE INVENTION

The present invention relates to a treatment for glaucoma. While the present invention does not depend on an understanding of the mechanism by which successful treatment is accomplished, it is believed that caldesmon disrupts the system of focal adhesions and actin and myosin II containing stress fibers, in turn causing changes in cell shape that translate into an increase in aqueous humor outflow facility.

It will be understood, that the use of a genetic construct to provide caldesmon to an eye of a subject, is considered a desired but not an essential aspect of the administration method. Vectors that are particularly well suited for introduction into non-dividing cells (of which trabecular meshwork cells are an example) are known and are considered desirable for in vivo expression of caldesmon in vivo in human and non-human animal eyes. A suitable vector can include an adenovirus vector, an adeno-associated virus vector, a herpes simplex virus-based vector, a lentivirus vector, and a plasmid vector. The skilled artisan will appreciate the importance of engineering a vector and its components for efficient use in trabecular meshwork cells. The transduction efficiency of the various delivery systems is known to vary and can depend upon the nature of the vector and its components.

In addition to vectors of the types noted above, non-vector approaches, including direct administration of caldesmon protein, liposomal delivery of caldesmon, and diffusion of caldesmon protein from implanted cells encapsulated in a sealed semipermeable membrane capsule, are contemplated.

The use of adenovirus expression vectors and other vector systems for therapeutic transfer of a nucleic acid construct into target tissue to treat glaucoma is described generally in, e.g., Borras, T. et al., "Gene Therapy for Glaucoma: Treating a Multifaceted, Chronic Disease," IOVS, 43:2513 (2002) and papers cited therein in references 25–31, each of which is incorporated by reference herein as if set forth in its entirety. Also incorporated herein by reference in its entirety is Hauswirth, W. W. and L. Beaufrere, "Ocular Gene Therapy: Quo Vadis?," IOVS 41:2821 (2000) which reviews the eye as a gene therapy target and concludes that "ocular gene therapy seems well poised to be among the earliest successful applications" of the technology. The cited papers also provide the skilled artisan with the technical requirements for a suitable expression vector.

The skilled person will appreciate that when a caldesmon-encoding genetic construct is delivered, various aspects can affect expression of caldesmon from the encoding construct. For example, the vector backbone of the genetic construct should be suited for efficient transfer into the target trabecular meshwork cells, for long-term maintenance of the construct in the cells and for sustained expression of caldesmon in the cells. Expression is sustained, e.g., by providing on the construct a transcriptional promoter that supports transcription in target trabecular meshwork cells. In particular, certain lentivirus vectors, namely certain feline immunodeficiency virus vectors, are efficiently transduced into human and non-human trabecular meshwork cells and provide efficient and long-term stable expression of a protein encoded by a polynucleotide provided on the vector. Suitable vectors, and methods for their production and use, are described in Loewen, N., et al., "Long-Term, Targeted Genetic Modification of the Aqueous Humor Outflow Tract Coupled with Noninvasive Imaging of Gene Expression In Vivo," IOVS, 45:3091 (2004) and in Loewen, N., et al., "Preservation of Aqueous Outflow Facility after Second-Generation FIV Vector-Mediated Expression of Marker Genes in Anterior Segments of Human Eyes," IOVS, 43:3686 (2002), each of which is incorporated by reference as if set forth herein in its entirety. Further incorporation by reference is made to the papers cited in the foregoing papers in connection with various starting materials and methods for producing vectors suited for efficient transduction into trabecular meshwork cells. Loewen, N., et al. (2004) provides the skilled person with guidance as to the amount of vector advantageously administered in vivo to cats, a species for which effectiveness of a therapeutic method is generally considered to be a reliable predictor of effectiveness of the method in humans. In cats, amounts in the range of between about $10^6$ and $10^8$ tranducing units (TU) were administered per eye with good results. The skilled person applying only routine skill can adjust these amounts, if appropriate, to deliver IOP-reducing amounts of vectors to anterior portions of the eye of human or other non-human subjects. Production of lentiviral vectors and delivery into non-dividing human eye cells is also described and claimed in U.S. Pat. No. 6,555,107, incorporated herein by reference as if set forth in its entirety.

Using conventional tools of the molecular biologist, the aforementioned vectors and others, can be modified to provide a polynucleotide that encodes caldesmon in the vector downstream from a transcriptional promoter functional in trabecular meshwork cells, such that caldesmon is produced in the TM cells.

In the accompanying working examples, caldesmon was encoded by and expressed from a vector in trabecular meshwork cells grown in culture or maintained in anterior segments mounted on organ perfusion culture dishes. In the examples, caldesmon and a marker, green fluorescent protein (GFP), were expressed upon introduction into the cells of an adenovirus expression vector under transcriptional control of a cytomegalovirus promoter-enhancer. Introduction by injection of genetic material is considered a preferred approach by the inventors, although provision of caldesmon protein to trabecular meshwork cells in a manner known to the art is also suitable.

The skilled artisan will appreciate that in due course further improvements to nucleic acid delivery methods, employing virus- or non-virus based approaches may be developed, and that the invention is sufficiently broad to encompass use of any such methods for providing caldesmon in trabecular meshwork cells, without regard to the specific delivery vector or method. Further, the caldesmon protein need not be obtained from a human or from a rat. As the activities of caldesmon are well understood, the skilled artisan can readily select a caldesmon protein source having the characteristic properties of caldesmon, namely actin-, myosin-, tropomyosin-, and $Ca^{2+}$-calmodulin-binding domains, or a nucleic acid sequence encoding same, for administration in the methods of the invention. It will also be understood that the ability of caldesmon to function in the methods of the invention may be modulated, particularly enhanced, by introducing one or more changes to amino acid residues of the caldesmon protein. The skilled artisan can introduce such changes at the nucleic acid level and can monitor outflow facility directed by modified proteins such that modified caldesmon proteins that yield great outflow facility (and nucleic acids encoding same) can be selected for use in the methods. The present invention will be more fully understood upon consideration of the following non-limiting examples. The examples demonstrate proof of principle, but the skilled artisan will appreciate that the caldesmon can be administered via any medically acceptable route. The examples are not intended to be limiting on the scope of the invention which embraces all such variations and modifications as fall within the scope of the appended claims.

EXAMPLES

Example One

Construction of a Replication Deficient Adenoviral Vector Encoding Caldesmon AdGFPCald, a recombinant, replication-deficient adenovirus carrying the linked coding cDNAs of GFP and non-muscle rat caldesmon was obtained by homologous recombination. The expression cassette cDNA of this recombinant virus contains a fusion of a cDNA that encodes GFP (nucleotides 284–1001 of GenBank Accession Number U76561) with the coding region of the rat caldesmon cDNA. The expression cassette of 2,323 nucleotides is flanked by a PmeI site at the 5' and a BamH1 site at the 3'; it also contains a 6 nucleotide XbaI site between the cDNA that encodes the two proteins.

The expression cassette was obtained by PCR amplification of plasmid pGFPcad [Helfman et al., M. B. C. 10:3097 (1999), incorporated supra] using forward 5'AGCTGTT-TAAACCACCATGGTGAGCAAGGGCGAGGAGCT3' (nucleotides 284–311 of GFP cDNA) (oligo # 243, SEQ ID NO:5) and reverse 5'ATGCGGATCCTCAGACCT-TAGTGGGAGAAGT3' (nucleotides 2318–2299 of rat caldesmon cDNA) (oligo # 244, SEQ ID NO:6) primers. The forward primer contains 4 extra nucleotide in its 5' plus a Pme I restriction site. The forward primer introduces the GFP natural Kozak sequences into the cassette and allows translation to start at the GFP ATG initiation codon. The reverse primer contains 4 extra nt in its 5' plus a Bam HI restriction site. The amplified insert was cloned into the pCR 2.1 vector (Invitrogen, San Diego, Calif.) (pJV10). The pJV10 plasmid insert was isolated by digestion of its cDNA with Pme I-Bam HI and subcloned into the pQBI-AdCMV5 shuttle vector (QBIOgene Montreal, Canada) which is under transcriptional control of CMV5, a cytomegalovirus (CMV) promoter-enhancer combination optimized for constitutive recombinant protein expression. The pQBI-AdCMV5 vector contains the β-globin polyadenylation (polyA) sequences. The pQBI-AdCMV5 also contains Ad5 sequences 1–194 (inverted terminal repeat, ITR) that provide the recombinant adenovirus left terminus and Ad5 map units 9.4–15.5 for overlap recombination.

The resulting shuttle plasmid, pAd-GFPCald (pJV1), was linearized with Cla I and co-transfected with an Ad5 viral DNA arm into 293 cells by calcium phosphate/DNA co-precipitation. The viral arm, QBI-viral DNA (QBIOgene, Montreal, Canada), is derived from Adenovirus serotype 5, subtype d1327 with deletions at the E1a and E3 genes. This arm is produced by cutting the DNA from adenovirus Ad5.CMVLacZΔE1/ΔE3 with Cla I and isolation of the 27 kb fragment lacking the left ITR and the LacZ cassette.

DNA precipitates of the pAd-GFPCald and QBI-viral DNA were exposed to the 293 cells for 12 h, washed exhaustively and allowed to recombine for two weeks. After recombination, harvested cells were lysed and their supernatant assayed for plaque purification by agar overlay {Borrás T., et al., "Ocular adenovirus gene transfer varies in efficiency and inflammatory response," *Invest Ophthalmol Vis Sci,* 37:1282–1293 (1996); Borrás T., et al., "Gene transfer to the human trabecular meshwork by anterior segment perfusion," *Invest Ophthalmol Vis Sci,* 39:1503–1507 (1998); Borrás T., et al., "Adenoviral reporter gene transfer to the human trabecular meshwork does not alter aqueous humor outflow. Relevance for potential gene therapy of glaucoma," *Gene Ther* 6: 515–524 (1999), each incorporated herein by reference as if set forth in its entirety).

Three GFP positive viral plaques were amplified and re-plated by agar overlay for second plaque purification. GFP positive plaque #2/#1 was selected to obtain a higher titer viral stock. A purified viral stock of AdGFPCald (plaque #2/#1) was obtained by propagation in 293 cells and was purified by double-banding in CsCl density gradients as described in the incorporated papers. Purified viruses were titered by the agar overlay plaque assay in 293 cells. This viral stock (lot# 010701) had a titer of $2.5 \times 10^{10}$ particle forming units (pfu) per ml in a formulation vehicle of 0.01 M Tris pH 8, 0.01 M $MgCl_2$ and 10% glycerol Absence of contaminant wild-type viruses in lot # 010701 was tested by PCR amplification with E1A primers 5'TCGAAGAGGTACTGGCTGAT3' (SEQ ID NO:7) and 5'TGACAAGACCTGCAACCGTG3' (SEQ ID NO:8).

For sequence confirmation of the recombinant AdGFP-Cald virus, a fragment containing its expression cassette was amplified from the its DNA with oligonucleotides 5'-GC-CCTCCCATATGTCCTTCCGAGTGAGAG-3' (606–634 nt in pQBI-AdCMV5 DNA) (oligo # 165, SEQ ID NO:9) and 5'-GGATTTGATATTCACCTGGCCCGATCTGG-3' (815–788 nt in pQBI-AdCMV5 DNA) (oligo # 164, SEQ ID NO:10). The ends of the isolated fragment were sequenced with above external oligonucleotides #165 and #164, reading approximately 700 nt each. Internal sequence was obtained with forward oligos 5'-GATCACTCTCGGCATG-GACGA-3' (975–995 nt in GFP cDNA) (oligo#245, SEQ ID NO:11), 5'-GATTTACAGAAGTGAAGGCGC-3' (1397–1415 in Caldesmon cDNA) (oligo#248, SEQ ID NO:12) and reverse oligos 5'-ACTGTTCTGGACATGGGCCTC-3' (924–904 in Caldesmon cDNA) (oligo# 247, SEQ ID NO:13) and 5'-CCTTTCGATCTCTTCCTTCAACC-3' (1470–1397 in caldesmon cDNA) (oligo#246, SEQ ID NO:14). No mismatches were found to referred sequences with the exception of a potential change of an Alanine to a Valine at amino acid 68 of the caldesmon protein.

Example Two

Use of Caldesmon to Alter Human Trabecular Meshwork (HTM) Cytoskeleton

Primary HTM cells grown on coverslips were infected with the AdGFPCald adenovirus vector of Example One at different multiplicities of infection, fixed and assayed by immunofluorescence staining of cytoskeletal proteins 24–48 h post-infection. SV40-transformed HTM cells were plated in glass bottom dishes, AdGFPCald infected, and examined by live time-lapse recording with an Axiovert 100 TV microscope.

Caldesmon co-localized with all actin-containing structures. High caldesmon overexpression induced severe changes in the actin cytoskeleton and formation of new type of actin structures such as curvy fiber networks. In these cells, focal adhesions were disrupted. HTM cells containing lower levels of recombinant caldesmon induced different and milder changes with shorter stress fibers and triangular structures. Real-time GFP-caldesmon dynamics showed motile curvy fibers undergoing continuous remodeling (fusion, formation of loops etc). Myosin remained associated with the altered actin structures in the caldesmon-overexpressing cells.

Recombinant caldesmon induced changes in the HTM cytoskeleton in a dose-dependent manner. This result suggests that modulation of caldesmon expression in the human trabecular meshwork can be used therapeutically to increase aqueous humor outflow facility and to reduce intraocular pressure in glaucoma.

Example Three

Use of Caldesmon to Improve Outflow Facility From Organ-Cultured Human and Monkey Anterior Segments Organ cultures of human and monkey eye anterior segments are widely regarded as a preferred system for evaluating and for establishing utility in vivo of proposed human therapeutic modalities. The details of the culture methods and several underlying literature citations are set forth in incorporated U.S. Pat. No. 6,586,425.

Six human and eight rhesus or cynomolgus monkey paired anterior segments were mounted on organ culture dishes and perfused with DMEM at a constant rate of 2.5 μl/min. For human eyes, baseline OF [flow divided by intraocular pressure (IOP)] was calculated after 24 hours of equilibration. Human anterior segments were injected with a single $10^7$ pfu dose of the AdGFPCald adenoviral vector of Example One to one eye; vehicle to the opposite eye. IOP was monitored continuously for 66 hours and average OF calculated every 6 hours. For monkey segments, baseline OF was determined by two-level constant pressure perfusion for 45–60 min after overnight equilibration. Segments were then injected via the infusion tubing with 20 ul containing $7.5 \times 10^8$ pfu/ml AdGFP to one eye; AdGFPCald to the opposite eye. Post-treatment OF was monitored at days 2, 5–6, and in some cases up to 9 days after injection. Human and monkey segments were embedded in OCT optimum cutting temperature cryoembedding matrix (Miles Scientific) and examined for the presence of fluorescence.

Baseline OF (μl/min/mmHg) was no different between the paired eyes, and averaged (mean±sem): human, 0.20±0.03 (n=11); monkey, 0.41±0.04 (n=16). In humans, the IOP began to decrease in AdGFPCald segments within 10 hours after the injection and continued to decrease for the duration of the 66 hours. The percent change of final OF from baseline was 49.0±24.8% (AdGFPCald) (p<0.09) and 0.6±7.8% (vehicle) (p<0.9). In monkey segments, the OF increase was detected as early as 1 day after the initial injection with the maximum OF increase occurring from 1 to 9 days after injection. When all eyes were considered, the mean maximum OF increase in AdGFPCald vs AdGFP eyes corrected for baseline was 101±19% (p<0.005). 3 of 8 segments appeared to be contaminated by days 5–6, although an increase in OF was noted before the contamination became apparent in 1 of the 3 segments; the other 2 segments were not tested. Fluorescence was present in both paired segments of monkey eyes and in the AdGFPCald segment of human eyes.

Caldesmon gene therapy can increase outflow facility in the human and monkey anterior segments in organ culture and has the potential to be used in vivo to control IOP in humans.

Example Four (Prophetic)

Use of Caldesmon to Improve Outflow Facility From Trabecular Meshwork in an Eye of a Living Subject An expressible genetic construct encoding caldesmon protein is delivered (or caldesmon protein is administered) to an eye of a human or a non-human subject having reduced outflow facility and elevated intraocular pressure in an amount effective to improve outflow facility and reduce intraocular pressure. Reduced outflow facility and elevated intraocular pressure can be characteristic of glaucoma in a subject. The delivery or administration is achieved in a manner effective to bring caldesmon into contact with the trabecular meshwork of the eye. The amount of material administered in the method can vary depending upon whether the caldesmon is administered as a protein or as a nucleic acid capable of encoding the caldesmon protein. In either case, the amount of caldesmon present in the trabecular meshwork after administration and effective in the method can be in the same order of magnitude as the agents disclosed in incorporated U.S. Pat. No. 6,586,425. Likewise, caldesmon can be administered in amounts comparable to those administered in the cited patent.

Upon administration, outflow facility is increased and intraocular pressure is reduced relative to pre-administration levels.

Example Five (Prophetic)

Use of Caldesmon to Improve Outflow Facility from Trabecular Meshwork in an Eye of a Living Subject An expressible FIV genetic construct encoding caldesmon protein is delivered in an amount between about $10^6$ and $10^8$ transducing units to trabecular meshwork cells in an eye of a human or a non-human subject having reduced outflow facility and elevated intraocular pressure. Reduced outflow facility and elevated intraocular pressure can be characteristic of glaucoma in a subject. Upon administration, outflow facility is increased and intraocular pressure is reduced relative to pre-administration levels.

The preceding examples are not intended to limit the scope of the invention, which encompasses all such modifications and variations as fall within the scope of the appended claims.

We claim:

1. A method for increasing outflow facility of aqueous humor from an eye having a trabecular meshwork, the method comprising the step of:
   providing to the trabecular meshwork of a subject in need of increased outflow facility an amount of caldesmon effective to increase outflow facility.

2. A method as claimed in claim 1, wherein the providing step includes the step of administering a pharmaceutical preparation comprising a non-corneotoxic delivery vehicle and the caldesmon protein to the trabecular meshwork in an amount effective to increase aqueous humor outflow facility from the eye.

3. A method as claimed in claim 1, wherein the caldesmon protein has a sequence selected from the group consisting of SEQ ID NO:2 and SEQ ID NO:4.

* * * * *

SEQUENCE LISTING

<160> NUMBER OF SEQ ID NOS: 14

<210> SEQ ID NO 1
<211> LENGTH: 5233

```
<212> TYPE: DNA
<213> ORGANISM: Homo sapiens
<220> FEATURE:
<221> NAME/KEY: CDS
<222> LOCATION: (460)..(2838)

<400> SEQUENCE: 1
gatttcctga gcatgcctag ggaatgacag gcatctccac aggcaggctg catccacctt    60
ggctggggtg tcgtcattgg ctgcctatta gaaaaacgac aggacaatgc ataccaccgc   120
ctcccgactg taaacatagg ggatatgtgt tcacttagca tggacttctg ggaggggcca   180
aggaagggcg gtctggagtt ttattgaata gagcagtgtg tattcggctg cctgcctgcc   240
cgcctgcttg ctctctggct gtgctcctgc ttaaagaaat cagtccttcc tttccgactt   300
agtcctcggg aagaagtttc agactacaag gtatcattgg aacatttcaa gatcatcaaa   360
tcaaattcca cagggattgg tgaccaacca gaaggctcag acatctgatt gctgacctgt   420
ccagacatca tctggtctcc ctgaacctga atcacacc atg gat gat ttt gag       474
                                          Met Asp Asp Phe Glu
                                            1               5 cgt cgc aga gaa ctt aga agg caa aag agg gag gag atg cga ctc gaa     522
Arg Arg Arg Glu Leu Arg Arg Gln Lys Arg Glu Glu Met Arg Leu Glu
             10                  15                  20 gca gaa aga atc gcc tac cag agg aat gac gat gat gaa gag gag gca     570
Ala Glu Arg Ile Ala Tyr Gln Arg Asn Asp Asp Asp Glu Glu Glu Ala
         25                  30                  35 gcc cgg gaa cgg cgc cgc cga gcc cga cag gaa cgg ctg cgg cag aag     618
Ala Arg Glu Arg Arg Arg Arg Ala Arg Gln Glu Arg Leu Arg Gln Lys
     40                  45                  50 cag gag gaa gaa tcc ttg gga cag gtg acc gac cag gtg gag gtg aat     666
Gln Glu Glu Glu Ser Leu Gly Gln Val Thr Asp Gln Val Glu Val Asn
 55                  60                  65 gcc cag aac agt gtg cct gac gag gag gcc aag aca acc acc aca aac     714
Ala Gln Asn Ser Val Pro Asp Glu Glu Ala Lys Thr Thr Thr Thr Asn
 70                  75                  80                  85 act caa gtg gaa ggg gat gat gag gcc gca ttc ctg gag cgc ctg gct     762
Thr Gln Val Glu Gly Asp Asp Glu Ala Ala Phe Leu Glu Arg Leu Ala
                 90                  95                 100 cgg cgt gag gaa aga cgc caa aaa cgc ctt cag gag gct ctg gag cgg     810
Arg Arg Glu Glu Arg Arg Gln Lys Arg Leu Gln Glu Ala Leu Glu Arg
            105                 110                 115 cag aag gag ttc gac cca aca ata aca gat gca agt ctg tcg ctc cca     858
Gln Lys Glu Phe Asp Pro Thr Ile Thr Asp Ala Ser Leu Ser Leu Pro
        120                 125                 130 agc aga aga atg caa aat gac aca gca gaa aat gaa act acc gag aag     906
Ser Arg Arg Met Gln Asn Asp Thr Ala Glu Asn Glu Thr Thr Glu Lys
    135                 140                 145 gaa gaa aaa agt gaa agt cgc caa gaa aga tac gag ata gag gaa aca     954
Glu Glu Lys Ser Glu Ser Arg Gln Glu Arg Tyr Glu Ile Glu Glu Thr
150                 155                 160                 165 gaa aca gtc acc aag tcc tac cag aag aat gat tgg agg gat gct gaa    1002
Glu Thr Val Thr Lys Ser Tyr Gln Lys Asn Asp Trp Arg Asp Ala Glu
                170                 175                 180 gaa aac aag aaa gaa gac aag gaa aag gag gag gag gaa gag gag aag    1050
Glu Asn Lys Lys Glu Asp Lys Glu Lys Glu Glu Glu Glu Glu Glu Lys
            185                 190                 195 cca aag cga ggg agc att gga gaa aat cag gta gag gtg atg gtg gaa    1098
Pro Lys Arg Gly Ser Ile Gly Glu Asn Gln Val Glu Val Met Val Glu
        200                 205                 210 gag aaa aca act gaa agc cag gag gaa aca gtg gta atg tca tta aaa    1146
```

-continued

| | | | | | | | | | | | | | | |
|---|---|---|---|---|---|---|---|---|---|---|---|---|---|---|
| Glu | Lys | Thr | Thr | Glu | Ser | Gln | Glu | Thr | Val | Val | Met | Ser | Leu | Lys |
| | 215 | | | | 220 | | | | 225 | | | | | |

```
aat ggg cag atc agt tca gaa gag cct aaa caa gag gag agg gaa    1194
Asn Gly Gln Ile Ser Ser Glu Glu Pro Lys Gln Glu Glu Arg Glu
230             235             240             245 caa ggt tca gat gag att tcc cat cat gaa aag atg gaa gag gaa gac    1242
Gln Gly Ser Asp Glu Ile Ser His His Glu Lys Met Glu Glu Glu Asp
            250             255             260 aag gaa aga gct gag gca gag agg gca agg ttg gaa gca gaa gaa aga    1290
Lys Glu Arg Ala Glu Ala Glu Arg Ala Arg Leu Glu Ala Glu Glu Arg
                265             270             275 gaa aga att aaa gcc gag caa gac aaa aag ata gca gat gaa cga gca    1338
Glu Arg Ile Lys Ala Glu Gln Asp Lys Lys Ile Ala Asp Glu Arg Ala
        280             285             290 aga att gaa gca gaa gaa aaa gca gct gcc caa gaa aga gaa agg aga    1386
Arg Ile Glu Ala Glu Glu Lys Ala Ala Ala Gln Glu Arg Glu Arg Arg
    295             300             305 gag gca gaa gag agg gaa agg atg agg gag gaa gag aaa agg gca gca    1434
Glu Ala Glu Glu Arg Glu Arg Met Arg Glu Glu Glu Lys Arg Ala Ala
310             315             320             325 gag gag agg cag agg ata aag gag gaa gag aaa agg gca gca gag gag    1482
Glu Glu Arg Gln Arg Ile Lys Glu Glu Glu Lys Arg Ala Ala Glu Glu
            330             335             340 agg cag agg ata aag gag gaa gag aaa agg gca gca gag gag agg cag    1530
Arg Gln Arg Ile Lys Glu Glu Glu Lys Arg Ala Ala Glu Glu Arg Gln
                345             350             355 agg ata aaa gag gaa gag aaa agg gca gca gag gag agg caa agg gcc    1578
Arg Ile Lys Glu Glu Glu Lys Arg Ala Ala Glu Glu Arg Gln Arg Ala
        360             365             370 agg gca gag gag gaa gag aag gct aag gta gaa gag cag aaa cgt aac    1626
Arg Ala Glu Glu Glu Glu Lys Ala Lys Val Glu Glu Gln Lys Arg Asn
    375             380             385 aag cag cta gaa gag aaa aaa cat gcc atg caa gag aca aag ata aaa    1674
Lys Gln Leu Glu Glu Lys Lys His Ala Met Gln Glu Thr Lys Ile Lys
390             395             400             405 ggg gaa aag gta gaa cag aaa ata gaa ggg aaa tgg gta aat gaa aag    1722
Gly Glu Lys Val Glu Gln Lys Ile Glu Gly Lys Trp Val Asn Glu Lys
            410             415             420 aaa gca caa gaa gat aaa ctt cag aca gct gtc cta aag aaa cag gga    1770
Lys Ala Gln Glu Asp Lys Leu Gln Thr Ala Val Leu Lys Lys Gln Gly
                425             430             435 gaa gag aag gga act aaa gtg caa gct aaa aga gaa aag ctc caa gaa    1818
Glu Glu Lys Gly Thr Lys Val Gln Ala Lys Arg Glu Lys Leu Gln Glu
        440             445             450 gac aag cct acc ttc aaa aaa gaa gag atc aaa gat gaa aag att aaa    1866
Asp Lys Pro Thr Phe Lys Lys Glu Glu Ile Lys Asp Glu Lys Ile Lys
    455             460             465 aag gac aaa gaa ccc aaa gaa gaa gtt aag agc ttc atg gat cga aag    1914
Lys Asp Lys Glu Pro Lys Glu Glu Val Lys Ser Phe Met Asp Arg Lys
470             475             480             485 aag gga ttt aca gaa gtt aag tcg cag aat gga gaa ttc atg acc cac    1962
Lys Gly Phe Thr Glu Val Lys Ser Gln Asn Gly Glu Phe Met Thr His
            490             495             500 aaa ctt aaa cat act gag aat act ttc agc cgc cct gga ggg agg gcc    2010
Lys Leu Lys His Thr Glu Asn Thr Phe Ser Arg Pro Gly Gly Arg Ala
                505             510             515 agc gtg gac acc aag gag gct gag ggc gcc ccc cag gtg gaa gcc ggc    2058
Ser Val Asp Thr Lys Glu Ala Glu Gly Ala Pro Gln Val Glu Ala Gly
        520             525             530
```

```
aaa agg ctg gag gag ctt cgt cgt cgt cgc ggg gag acc gag agc gaa      2106
Lys Arg Leu Glu Glu Leu Arg Arg Arg Arg Gly Glu Thr Glu Ser Glu
535                 540                 545 gag ttc gag aag ctc aaa cag aag cag cag gag gcg gct ttg gag ctg      2154
Glu Phe Glu Lys Leu Lys Gln Lys Gln Gln Glu Ala Ala Leu Glu Leu
550                 555                 560                 565 gag gaa ctc aag aaa aag agg gag gag aga agg aag gtc ctg gag gag      2202
Glu Glu Leu Lys Lys Lys Arg Glu Glu Arg Arg Lys Val Leu Glu Glu
                570                 575                 580 gaa gag cag agg agg aag cag gag gaa gcc gat cga aaa ctc aga gag      2250
Glu Glu Gln Arg Arg Lys Gln Glu Glu Ala Asp Arg Lys Leu Arg Glu
            585                 590                 595 gag gaa gag aag agg agg cta aag gaa gag att gaa agg cga aga gca      2298
Glu Glu Glu Lys Arg Arg Leu Lys Glu Glu Ile Glu Arg Arg Arg Ala
        600                 605                 610 gaa gct gct gag aaa cgc cag aag atg cca gaa gat ggc ttg tca gat      2346
Glu Ala Ala Glu Lys Arg Gln Lys Met Pro Glu Asp Gly Leu Ser Asp
    615                 620                 625 gac aag aaa cca ttc aag tgt ttc act cct aaa ggt tca tct ctc aag      2394
Asp Lys Lys Pro Phe Lys Cys Phe Thr Pro Lys Gly Ser Ser Leu Lys
630                 635                 640                 645 ata gaa gag cga gca gaa ttt ttg aat aag tct gtg cag aaa agc agt      2442
Ile Glu Glu Arg Ala Glu Phe Leu Asn Lys Ser Val Gln Lys Ser Ser
                650                 655                 660 ggt gtc aaa tcg acc cat caa gca gca ata gtc tcc aag att gac agc      2490
Gly Val Lys Ser Thr His Gln Ala Ala Ile Val Ser Lys Ile Asp Ser
            665                 670                 675 aga ctg gag cag tat acc agt gca att gag gga aca aaa agc gca aaa      2538
Arg Leu Glu Gln Tyr Thr Ser Ala Ile Glu Gly Thr Lys Ser Ala Lys
        680                 685                 690 cct aca aag ccg gca gcc tcg gat ctt cct gtt cct gct gaa ggt gta      2586
Pro Thr Lys Pro Ala Ala Ser Asp Leu Pro Val Pro Ala Glu Gly Val
    695                 700                 705 cgc aac atc aag agt atg tgg gag aaa ggg aat gtg ttt tca tcc ccc      2634
Arg Asn Ile Lys Ser Met Trp Glu Lys Gly Asn Val Phe Ser Ser Pro
710                 715                 720                 725 act gca gca ggc aca cca aat aag gaa act gct ggc ttg aag gta ggg      2682
Thr Ala Ala Gly Thr Pro Asn Lys Glu Thr Ala Gly Leu Lys Val Gly
                730                 735                 740 gtt tct agc cgc atc aat gaa tgg cta act aaa acc cca gat gga aac      2730
Val Ser Ser Arg Ile Asn Glu Trp Leu Thr Lys Thr Pro Asp Gly Asn
            745                 750                 755 aag tca cct gct ccc aaa cct tct gac ttg aga cca gga gac gta tcc      2778
Lys Ser Pro Ala Pro Lys Pro Ser Asp Leu Arg Pro Gly Asp Val Ser
        760                 765                 770 agc aag cgg aac ctc tgg gaa aag caa tct gtg gat aag gtc act tcc      2826
Ser Lys Arg Asn Leu Trp Glu Lys Gln Ser Val Asp Lys Val Thr Ser
    775                 780                 785 ccc act aag gtt tgagacagtt ccagaaagaa cccaagctca agacgcagga         2878
Pro Thr Lys Val
790 cgagctcagt tgtagagggc taattcgctc tgttttgtat ttatgttgat ttactaaatt   2938 gggttcatta tcttttattt ttcaatatcc cagtaaaccc atgtatatta tcactatatt   2998 taataatcac agtctagaga tgttcatggt aaaagtactg cctttgcaca ggagcctgtt   3058 tctaaagaaa cccatgctgt gaaatagaga cttttctact gatcatcata actctgtatc   3118 tgagcagtga taccaaccac atctgaagtc aacagaagat ccaagtttaa aattgcctgc   3178 ggaatgtgtg cagtatctag aaaaatgaac cgtagttttt gttttttttaa atacagaagt   3238
```

```
catgttgttt ctgcactttta taataaagca tggaagaaat tatcttagta ggcaattgta    3298
acactttttg aaagtaaccc atttcagatt tgaaatactg caataatggt tgtctttaaa    3358
aaaaaaaaag aaatgtactg ttaaggtatt acttttttc atgctgatga ttcatatcta    3418
aattacatta ttatgttagc tgacagtggt actgattttt taggttggtt gttttgtgga    3478
tttctttagt agtgatagta gcctgaacca cattttagat aactcaatta tgtatgtatg    3538
tgcatacaca tatacaaaca cactaatggt agaatgcttt tttatgtgct agactattat    3598
atttagtagt atgtcattgt aactagccaa atcacagct tttgaaaaat taaaaaatca     3658
cactatatta atatttcata tttgccaaca gaaacatggc agataggtat caatatgttt    3718
tcaatgcctg atgacctata agaagaaagt attgaaaaga agagagatta gaactgttag    3778
aaggagttga aattttctaa aagacatagt atttagttta taattaaatg cattcttgaa    3838
gtccagtgtg aattttatta atgctatcat ctcgaccaag ctcaaagcct acttattaga    3898
aacaatgaag ttcacaatag gtcataaggt ctcttccttt tctaaaattg aaagacaaga    3958
aatttagtgc caatattgta cagacagaaa ttccatgtat gagtctcaac aaagactacc    4018
tttggctaaa tgtctagaag cagagaagta aagtgagcaa atccagtgt tgaggagtca     4078 tgacagtact ttgatcttta tatactctga agcatttctt caaactttc tactttttatt     4138 tgtcattgat acctgtagta agttgacaat gtggtgaaat ttcaaaatta tatgtaactt    4198
ctactagttt tactttctcc cccaagtctt ttttaactca tgatttttac acacacaatc    4258
cagaacttat tatatagcct ctaagtcttt attcttcaca gtagataatg aaagagtcct    4318
ccagtgtctt ggcaaaatgt tctagtatag ctggatacat acagtggagt tctataaact    4378
catacctcag tggacttaac caaaattgtg ttagtctcaa ttcctaccac actgagggag    4438
cctcccaaat aactatttc ttatctgcag tattcctcca gaagagctaa ccagggcagg      4498
gctggcatga gaagtgacat ctgcgttaca agtctatct tcctcataag tctgtaaaga      4558
gcaattgaat cttctagctt tagcaaacct aagccaaagg aaggaaagcc acgaagaatg    4618
cagaagtcaa accctcatga caaagtaggc acaagtctac aataagctaa atcagaattt    4678
acaaatacaa gtgtcccagg tagcattgac tcccgtcatt ggagtgaaat ggatcaaagt    4738
ttgaattaag gcctatggta aggtaacatt gctttgttgt acttttgaac aagagctcct    4798
cctgatcact attacatatt tttctagaaa atctaaagtt cagaagagaa tgtatcactg    4858
ctgactttta ttccaatatt tggatggagt aagttttagg gtagaatttt gttcagtttg    4918
gatttaatct tttgaaaagt aaattccttg tttactggtt tgactataat tctctgttat    4978
ctttacgagg taaaactgca agctgactag catgttctgt gaatctgcca ttcctaaaaa    5038
ttttataaac acttgatact tttcactgat aatggatcgc tccaataaac atatattgtg    5098
aaaatgcatc cacaataaat ggaattcctt cctgcaaaat gtcttttct cacttatttt     5158 tatgtacaat attgatagtg agaggtatgt ctattataat aaagattatg gcacagtaaa    5218 aaaaaaaaa aaaaa                                                      5233
```

<210> SEQ ID NO 2
<211> LENGTH: 793
<212> TYPE: PRT
<213> ORGANISM: Homo sapiens

<400> SEQUENCE: 2

Met Asp Asp Phe Glu Arg Arg Arg Glu Leu Arg Arg Gln Lys Arg Glu
1               5                   10                  15

-continued

Glu Met Arg Leu Glu Ala Glu Arg Ile Ala Tyr Gln Arg Asn Asp Asp
            20                  25                  30

Asp Glu Glu Glu Ala Ala Arg Glu Arg Arg Arg Ala Arg Gln Glu
            35                  40                  45

Arg Leu Arg Gln Lys Gln Glu Glu Ser Leu Gly Gln Val Thr Asp
            50                  55                  60

Gln Val Glu Val Asn Ala Gln Asn Ser Val Pro Asp Glu Glu Ala Lys
 65                  70                  75                  80

Thr Thr Thr Thr Asn Thr Gln Val Glu Gly Asp Asp Glu Ala Ala Phe
                     85                  90                  95

Leu Glu Arg Leu Ala Arg Arg Glu Glu Arg Arg Gln Lys Arg Leu Gln
            100                 105                 110

Glu Ala Leu Glu Arg Gln Lys Glu Phe Asp Pro Thr Ile Thr Asp Ala
            115                 120                 125

Ser Leu Ser Leu Pro Ser Arg Arg Met Gln Asn Asp Thr Ala Glu Asn
            130                 135                 140

Glu Thr Thr Glu Lys Glu Glu Lys Ser Glu Ser Arg Gln Glu Arg Tyr
145                 150                 155                 160

Glu Ile Glu Glu Thr Glu Thr Val Thr Lys Ser Tyr Gln Lys Asn Asp
                    165                 170                 175

Trp Arg Asp Ala Glu Glu Asn Lys Lys Glu Asp Lys Glu Lys Glu Glu
            180                 185                 190

Glu Glu Glu Glu Lys Pro Lys Arg Gly Ser Ile Gly Glu Asn Gln Val
            195                 200                 205

Glu Val Met Val Glu Glu Lys Thr Thr Glu Ser Gln Glu Glu Thr Val
            210                 215                 220

Val Met Ser Leu Lys Asn Gly Gln Ile Ser Ser Glu Glu Pro Lys Gln
225                 230                 235                 240

Glu Glu Glu Arg Glu Gln Gly Ser Asp Glu Ile Ser His His Glu Lys
                    245                 250                 255

Met Glu Glu Glu Asp Lys Glu Arg Ala Glu Ala Glu Arg Ala Arg Leu
            260                 265                 270

Glu Ala Glu Glu Arg Glu Arg Ile Lys Ala Glu Gln Asp Lys Lys Ile
            275                 280                 285

Ala Asp Glu Arg Ala Arg Ile Glu Ala Glu Glu Lys Ala Ala Ala Gln
            290                 295                 300

Glu Arg Glu Arg Arg Glu Ala Glu Glu Arg Glu Arg Met Arg Glu Glu
305                 310                 315                 320

Glu Lys Arg Ala Ala Glu Glu Arg Gln Arg Ile Lys Glu Glu Glu Lys
            325                 330                 335

Arg Ala Ala Glu Glu Arg Gln Arg Ile Lys Glu Glu Lys Arg Ala
            340                 345                 350

Ala Glu Glu Arg Gln Arg Ile Lys Glu Glu Lys Arg Ala Ala Glu
            355                 360                 365

Glu Arg Gln Arg Ala Arg Ala Glu Glu Glu Lys Ala Lys Val Glu
            370                 375                 380

Glu Gln Lys Arg Asn Lys Gln Leu Glu Glu Lys Lys His Ala Met Gln
385                 390                 395                 400

Glu Thr Lys Ile Lys Gly Glu Lys Val Glu Gln Lys Ile Glu Gly Lys
                    405                 410                 415

Trp Val Asn Glu Lys Lys Ala Gln Glu Asp Lys Leu Gln Thr Ala Val
            420                 425                 430

```
Leu Lys Lys Gln Gly Glu Glu Lys Gly Thr Lys Val Gln Ala Lys Arg
            435                 440                 445

Glu Lys Leu Gln Glu Asp Lys Pro Thr Phe Lys Lys Glu Glu Ile Lys
        450                 455                 460

Asp Glu Lys Ile Lys Lys Asp Lys Glu Pro Lys Glu Glu Val Lys Ser
465                 470                 475                 480

Phe Met Asp Arg Lys Lys Gly Phe Thr Glu Val Lys Ser Gln Asn Gly
                485                 490                 495

Glu Phe Met Thr His Lys Leu Lys His Thr Glu Asn Thr Phe Ser Arg
            500                 505                 510

Pro Gly Gly Arg Ala Ser Val Asp Thr Lys Glu Ala Glu Gly Ala Pro
        515                 520                 525

Gln Val Glu Ala Gly Lys Arg Leu Glu Glu Leu Arg Arg Arg Arg Gly
530                 535                 540

Glu Thr Glu Ser Glu Glu Phe Glu Lys Leu Lys Gln Lys Gln Gln Glu
545                 550                 555                 560

Ala Ala Leu Glu Leu Glu Glu Leu Lys Lys Lys Arg Glu Glu Arg Arg
                565                 570                 575

Lys Val Leu Glu Glu Glu Glu Gln Arg Arg Lys Gln Glu Glu Ala Asp
            580                 585                 590

Arg Lys Leu Arg Glu Glu Glu Glu Lys Arg Arg Leu Lys Glu Glu Ile
        595                 600                 605

Glu Arg Arg Arg Ala Glu Ala Ala Glu Lys Arg Gln Lys Met Pro Glu
            610                 615                 620

Asp Gly Leu Ser Asp Asp Lys Lys Pro Phe Lys Cys Phe Thr Pro Lys
625                 630                 635                 640

Gly Ser Ser Leu Lys Ile Glu Glu Arg Ala Glu Phe Leu Asn Lys Ser
                645                 650                 655

Val Gln Lys Ser Ser Gly Val Lys Ser Thr His Gln Ala Ala Ile Val
            660                 665                 670

Ser Lys Ile Asp Ser Arg Leu Glu Gln Tyr Thr Ser Ala Ile Glu Gly
        675                 680                 685

Thr Lys Ser Ala Lys Pro Thr Lys Pro Ala Ala Ser Asp Leu Pro Val
            690                 695                 700

Pro Ala Glu Gly Val Arg Asn Ile Lys Ser Met Trp Glu Lys Gly Asn
705                 710                 715                 720

Val Phe Ser Ser Pro Thr Ala Ala Gly Thr Pro Asn Lys Glu Thr Ala
                725                 730                 735

Gly Leu Lys Val Gly Val Ser Ser Arg Ile Asn Glu Trp Leu Thr Lys
            740                 745                 750

Thr Pro Asp Gly Asn Lys Ser Pro Ala Pro Lys Pro Ser Asp Leu Arg
        755                 760                 765

Pro Gly Asp Val Ser Ser Lys Arg Asn Leu Trp Glu Lys Gln Ser Val
770                 775                 780

Asp Lys Val Thr Ser Pro Thr Lys Val
785                 790

<210> SEQ ID NO 3
<211> LENGTH: 2848
<212> TYPE: DNA
<213> ORGANISM: Rattus norvegicus
<220> FEATURE:
<221> NAME/KEY: CDS
<222> LOCATION: (156)..(1751)

<400> SEQUENCE: 3
```

-continued

```
agacccaagt gttaacacaa agggaagact ggcgcatcct gctcagcgca tttcggcaac      60
agataatatg gcccgtgtgc tggcccagcc catgctctga cctccaggcg ccaggtcccc     120
tacctcagtc actcctaccc agaccagctg cggac atg ctt agc aga tcc ggg       173
                                      Met Leu Ser Arg Ser Gly
                                       1               5 tcc cag gga agg cgc tgc ctg gcc aca ctc tct caa att gcc tat cag       221
Ser Gln Gly Arg Arg Cys Leu Ala Thr Leu Ser Gln Ile Ala Tyr Gln
         10                  15                  20 agg aat gat gat gac gaa gaa gag gct gcc agg gaa cgg cgc cgc cga       269
Arg Asn Asp Asp Asp Glu Glu Glu Ala Ala Arg Glu Arg Arg Arg Arg
             25                  30                  35 gcc cga cag gaa agg ctg cgg cag aag caa gag gaa gaa tcc ttg gga       317
Ala Arg Gln Glu Arg Leu Arg Gln Lys Gln Glu Glu Glu Ser Leu Gly
         40                  45                  50 cag gtg aca gac caa gtg gag gcc cat gtc cag aac agt gcc ccc gat       365
Gln Val Thr Asp Gln Val Glu Ala His Val Gln Asn Ser Ala Pro Asp
 55                  60                  65                  70 gaa gag tct aag cca gcc act gca aat gct cag gta gaa ggt gat gag       413
Glu Glu Ser Lys Pro Ala Thr Ala Asn Ala Gln Val Glu Gly Asp Glu
                 75                  80                  85 gag gct gct ttg ctg gag cgc ctg gcc agg cga gaa gag aga cgt caa       461
Glu Ala Ala Leu Leu Glu Arg Leu Ala Arg Arg Glu Glu Arg Arg Gln
             90                  95                 100 aaa cgc ctt cag gaa gcc tta gag cgt cag aag gag ttt gat cca acc       509
Lys Arg Leu Gln Glu Ala Leu Glu Arg Gln Lys Glu Phe Asp Pro Thr
        105                 110                 115 ata acc gat ggc agt ctc tca gtc cca agc aga agg atg caa aat aac       557
Ile Thr Asp Gly Ser Leu Ser Val Pro Ser Arg Arg Met Gln Asn Asn
        120                 125                 130 tcg gct gaa aat gag aca gca gag ggg gaa gaa aaa gga gag agt cgc       605
Ser Ala Glu Asn Glu Thr Ala Glu Gly Glu Glu Lys Gly Glu Ser Arg
135                 140                 145                 150 tca gga cgg tat gag atg gaa gaa aca gaa gtg gtc atc acg tcc tac       653
Ser Gly Arg Tyr Glu Met Glu Glu Thr Glu Val Val Ile Thr Ser Tyr
                155                 160                 165 cag aag aac agc tat cag gat gct gaa gac aaa aag aaa gaa gaa aag       701
Gln Lys Asn Ser Tyr Gln Asp Ala Glu Asp Lys Lys Lys Glu Glu Lys
            170                 175                 180 gag gag gag gag gag gaa gag aag ctg aag gga ggg aac ctt ggc gaa       749
Glu Glu Glu Glu Glu Glu Glu Lys Leu Lys Gly Gly Asn Leu Gly Glu
            185                 190                 195 aat cag atc aaa gat gag aag att aaa aag gac aaa gag ccc aaa gaa       797
Asn Gln Ile Lys Asp Glu Lys Ile Lys Lys Asp Lys Glu Pro Lys Glu
200                 205                 210 gaa gtc aag aac ttc ttg gat cga aag aaa gga ttt aca gaa gtg aag       845
Glu Val Lys Asn Phe Leu Asp Arg Lys Lys Gly Phe Thr Glu Val Lys
215                 220                 225                 230 gcg cag aat gga gaa ttc atg acc cac aaa ctt aaa caa act gag aat       893
Ala Gln Asn Gly Glu Phe Met Thr His Lys Leu Lys Gln Thr Glu Asn
                235                 240                 245 gct ttc agc ccc agc cgt tca gga ggc cgg gcc agc ggg gac aag gaa       941
Ala Phe Ser Pro Ser Arg Ser Gly Gly Arg Ala Ser Gly Asp Lys Glu
            250                 255                 260 gct gaa ggc gcc cca caa gtg gaa gcc ggt aag agg ctg gag gag ctg       989
Ala Glu Gly Ala Pro Gln Val Glu Ala Gly Lys Arg Leu Glu Glu Leu
        265                 270                 275 cgc cga cgc cgt ggg gag aca gag agc gaa gag ttc gaa aaa ctc aaa      1037
Arg Arg Arg Arg Gly Glu Thr Glu Ser Glu Glu Phe Glu Lys Leu Lys
```

```
            280                 285                 290
caa aag caa cag gag gca gcc ttg gag ctg gaa gag ctg aag aaa aag    1085
Gln Lys Gln Gln Glu Ala Ala Leu Glu Leu Glu Glu Leu Lys Lys Lys
295                 300                 305                 310 agg gaa gag aga agg aag gtt ctg gag gaa gag gag cag aga agg aag    1133
Arg Glu Glu Arg Arg Lys Val Leu Glu Glu Glu Glu Gln Arg Arg Lys
                315                 320                 325 cag gag gag gct gat cga aaa gct aga gag gag gaa gag aag agg agg    1181
Gln Glu Glu Ala Asp Arg Lys Ala Arg Glu Glu Glu Lys Arg Arg
            330                 335                 340 ttg aag gaa gag atc gaa agg aga agg gca gaa gct gct gag aaa cgc    1229
Leu Lys Glu Glu Ile Glu Arg Arg Arg Ala Glu Ala Ala Glu Lys Arg
        345                 350                 355 cag aag atg ccg gaa gat ggc cta tct gag gac aag aag ccg ttc aag    1277
Gln Lys Met Pro Glu Asp Gly Leu Ser Glu Asp Lys Lys Pro Phe Lys
    360                 365                 370 tgc ttc act cct aaa ggc tca tct ctc aag ata gag gag cga gca gag    1325
Cys Phe Thr Pro Lys Gly Ser Ser Leu Lys Ile Glu Glu Arg Ala Glu
375                 380                 385                 390 ttt ttg aat aag tct gtg cag aaa agt ggt gtc aaa tca act cat caa    1373
Phe Leu Asn Lys Ser Val Gln Lys Ser Gly Val Lys Ser Thr His Gln
                395                 400                 405 gca gct gtg gtc tcc aag att gac agc cgg ctg gag caa tat acc aat    1421
Ala Ala Val Val Ser Lys Ile Asp Ser Arg Leu Glu Gln Tyr Thr Asn
            410                 415                 420 gca atc gag gga aca aaa gct tca aaa cct atg aag cct gca gca tcc    1469
Ala Ile Glu Gly Thr Lys Ala Ser Lys Pro Met Lys Pro Ala Ala Ser
        425                 430                 435 gat ctt cct gtc cct gcg gaa ggt gtc cgc aat atc aag agc atg tgg    1517
Asp Leu Pro Val Pro Ala Glu Gly Val Arg Asn Ile Lys Ser Met Trp
    440                 445                 450 gag aaa ggg agt gtg ttt tca tcc ccc tct gcc tcg ggg aca cca aat    1565
Glu Lys Gly Ser Val Phe Ser Ser Pro Ser Ala Ser Gly Thr Pro Asn
455                 460                 465                 470 aag gaa act gct ggc ctg aag gtg ggg gtt tcc agc cgc atc aat gaa    1613
Lys Glu Thr Ala Gly Leu Lys Val Gly Val Ser Ser Arg Ile Asn Glu
                475                 480                 485 tgg cta act aaa tcg ccg gac ggc aac aag tca ccc gct ccc aag cct    1661
Trp Leu Thr Lys Ser Pro Asp Gly Asn Lys Ser Pro Ala Pro Lys Pro
            490                 495                 500 tct gac tta agg cca gga gat gta tct ggc aag cgg aac ctc tgg gaa    1709
Ser Asp Leu Arg Pro Gly Asp Val Ser Gly Lys Arg Asn Leu Trp Glu
        505                 510                 515 aag caa tcc gtg gat aag gtc act tct ccc act aag gtc tga            1751
Lys Gln Ser Val Asp Lys Val Thr Ser Pro Thr Lys Val
    520                 525                 530 aacaatcgga gaaagaaccc aactgcaagc catcttgctg ggccagctca gttggagagg  1811
gctaatcgct ctgtttatat ttatgttttc caatatccca gtaaattcat gtatatgctc  1871
actatattta ataaccacaa gtagaggtgt tcatggtcaa agtgctgcct ttgcagagga  1931
gcctgtttct aaagaaaccc atgctgtgaa gtaagcttgc tactgtcata tgaacagtga  1991
taccaaccac atcagaagtc gacaaaagaa aatcgagctt aagattgtcc aaggaatgta  2051
tgcggtatct aggtgggggg aaatgaccca taggctttgt tttgtctcag tacagacatc  2111
atgtttctgc actttagact aaagcatgga agaaattatc taagtaggca atcaaaattc  2171
tctgaaagtg atccacttca gatctgatat agggcagtga tgattgtctt ttttttaaa   2231 aaagaagatg tactgttgac atattgcttt tcttctatgc tgattcatac ctagattggg  2291
```

```
tgattattt  agctgacagt  ggtactgatt  tttttcttca  ggttagttgc  tttgtggatt      2351
tctctggtag  cgatagtaga  ctgaaccaca  tttagatata  acccaactat  gtaatgtatg      2411
tgcatacgtg  tatacagaca  cactaatggt  agatgactct  ttcatgctgg  cgctattcta      2471
tttcatagta  cgcccttgta  actaaccaat  atcacagctt  tcaaagatta  aagaaaatca      2531
caatagtata  tcaatatttc  atatttgcca  gtagaaacat  ggaagttagg  tatagatatg      2591
ttttcaatgc  ccaatgactt  ataagaaaaa  agtattggaa  aaataagaga  ttacaagtgt      2651
caaaactagt  tgaaacttct  tataagacat  agtatttagt  ttataattga  gagcagtctt      2711
gaattccagt  gtgaatttta  ttaagtctac  catctggaca  aagcccaaac  cctgttatt       2771 tgtggccgtg  aagttcacct  cctccacaca  caaaaaaagt  tgacctacat  gatacctaag      2831
gtgtctcctt  tctctac                                                         2848
```

<210> SEQ ID NO 4
<211> LENGTH: 531
<212> TYPE: PRT
<213> ORGANISM: Rattus norvegicus

<400> SEQUENCE: 4

```
Met Leu Ser Arg Ser Gly Ser Gln Gly Arg Arg Cys Leu Ala Thr Leu
1               5                   10                  15

Ser Gln Ile Ala Tyr Gln Arg Asn Asp Asp Glu Glu Ala Ala
            20                  25                  30

Arg Glu Arg Arg Arg Ala Arg Gln Glu Arg Leu Arg Gln Lys Gln
        35                  40                  45

Glu Glu Glu Ser Leu Gly Gln Val Thr Asp Gln Val Glu Ala His Val
    50                  55                  60

Gln Asn Ser Ala Pro Asp Glu Ser Lys Pro Ala Thr Ala Asn Ala
65                  70                  75                  80

Gln Val Glu Gly Asp Glu Ala Ala Leu Leu Glu Arg Leu Ala Arg
                85                  90                  95

Arg Glu Glu Arg Arg Gln Lys Arg Leu Gln Glu Ala Leu Glu Arg Gln
            100                 105                 110

Lys Glu Phe Asp Pro Thr Ile Thr Asp Gly Ser Leu Ser Val Pro Ser
        115                 120                 125

Arg Arg Met Gln Asn Asn Ser Ala Glu Asn Glu Thr Ala Glu Gly Glu
    130                 135                 140

Glu Lys Gly Glu Ser Arg Ser Gly Arg Tyr Glu Met Glu Glu Thr Glu
145                 150                 155                 160

Val Val Ile Thr Ser Tyr Gln Lys Asn Ser Tyr Gln Asp Ala Glu Asp
                165                 170                 175

Lys Lys Lys Glu Glu Lys Glu Glu Glu Glu Glu Lys Leu Lys
            180                 185                 190

Gly Gly Asn Leu Gly Glu Asn Gln Ile Lys Asp Glu Lys Ile Lys Lys
        195                 200                 205

Asp Lys Glu Pro Lys Glu Val Lys Asn Phe Leu Asp Arg Lys Lys
    210                 215                 220

Gly Phe Thr Glu Val Lys Ala Gln Asn Gly Glu Phe Met Thr His Lys
225                 230                 235                 240

Leu Lys Gln Thr Glu Asn Ala Phe Ser Pro Ser Arg Ser Gly Gly Arg
                245                 250                 255

Ala Ser Gly Asp Lys Glu Ala Glu Gly Ala Pro Gln Val Glu Ala Gly
            260                 265                 270
```

```
Lys Arg Leu Glu Glu Leu Arg Arg Arg Gly Glu Thr Glu Ser Glu
        275                 280                 285
Glu Phe Glu Lys Leu Lys Gln Lys Gln Gln Glu Ala Ala Leu Glu Leu
    290                 295                 300
Glu Glu Leu Lys Lys Lys Arg Glu Arg Arg Lys Val Leu Glu Glu
305                 310                 315                 320
Glu Glu Gln Arg Arg Lys Gln Glu Glu Ala Asp Arg Lys Ala Arg Glu
                325                 330                 335
Glu Glu Glu Lys Arg Arg Leu Lys Glu Glu Ile Glu Arg Arg Ala
                340                 345                 350
Glu Ala Ala Glu Lys Arg Gln Lys Met Pro Glu Asp Gly Leu Ser Glu
                355                 360                 365
Asp Lys Lys Pro Phe Lys Cys Phe Thr Pro Lys Gly Ser Ser Leu Lys
    370                 375                 380
Ile Glu Glu Arg Ala Glu Phe Leu Asn Lys Ser Val Gln Lys Ser Gly
385                 390                 395                 400
Val Lys Ser Thr His Gln Ala Ala Val Val Ser Lys Ile Asp Ser Arg
                405                 410                 415
Leu Glu Gln Tyr Thr Asn Ala Ile Glu Gly Thr Lys Ala Ser Lys Pro
                420                 425                 430
Met Lys Pro Ala Ala Ser Asp Leu Pro Val Pro Ala Glu Gly Val Arg
    435                 440                 445
Asn Ile Lys Ser Met Trp Glu Lys Gly Ser Val Phe Ser Ser Pro Ser
    450                 455                 460
Ala Ser Gly Thr Pro Asn Lys Glu Thr Ala Gly Leu Lys Val Gly Val
465                 470                 475                 480
Ser Ser Arg Ile Asn Glu Trp Leu Thr Lys Ser Pro Asp Gly Asn Lys
                485                 490                 495
Ser Pro Ala Pro Lys Pro Ser Asp Leu Arg Pro Gly Asp Val Ser Gly
            500                 505                 510
Lys Arg Asn Leu Trp Glu Lys Gln Ser Val Asp Lys Val Thr Ser Pro
    515                 520                 525
Thr Lys Val
    530

<210> SEQ ID NO 5
<211> LENGTH: 39
<212> TYPE: DNA
<213> ORGANISM: Synthetic DNA

<400> SEQUENCE: 5
agctgtttaa accaccatgg tgagcaaggg cgaggagct                    39

<210> SEQ ID NO 6
<211> LENGTH: 31
<212> TYPE: DNA
<213> ORGANISM: synthetic DNA

<400> SEQUENCE: 6
atgcggatcc tcagaccctta gtgggagaag t                           31

<210> SEQ ID NO 7
<211> LENGTH: 20
<212> TYPE: DNA
<213> ORGANISM: Synthetic DNA

<400> SEQUENCE: 7
```

```
tcgaagaggt actggctgat                                               20

<210> SEQ ID NO 8
<211> LENGTH: 20
<212> TYPE: DNA
<213> ORGANISM: Synthetic DNA

<400> SEQUENCE: 8
tgacaagacc tgcaaccgtg                                               20

<210> SEQ ID NO 9
<211> LENGTH: 29
<212> TYPE: DNA
<213> ORGANISM: Synthetic DNA

<400> SEQUENCE: 9
gccctcccat atgtccttcc gagtgagag                                     29

<210> SEQ ID NO 10
<211> LENGTH: 29
<212> TYPE: DNA
<213> ORGANISM: Synthetic DNA

<400> SEQUENCE: 10
ggatttgata ttcacctggc ccgatctgg                                     29

<210> SEQ ID NO 11
<211> LENGTH: 21
<212> TYPE: DNA
<213> ORGANISM: Synthetic DNA

<400> SEQUENCE: 11
gatcactctc ggcatggacg a                                             21

<210> SEQ ID NO 12
<211> LENGTH: 21
<212> TYPE: DNA
<213> ORGANISM: Synthetic DNA

<400> SEQUENCE: 12
gatttacaga agtgaaggcg c                                             21

<210> SEQ ID NO 13
<211> LENGTH: 21
<212> TYPE: DNA
<213> ORGANISM: Synthetic DNA

<400> SEQUENCE: 13
actgttctgg acatgggcct c                                             21

<210> SEQ ID NO 14
<211> LENGTH: 23
<212> TYPE: DNA
<213> ORGANISM: Synthetic DNA

<400> SEQUENCE: 14
cctttcgatc tcttccttca acc                                           23
```